United States Patent [19]
Sirney et al.

[11] Patent Number: 6,113,390
[45] Date of Patent: Sep. 5, 2000

[54] ORTHODONTIC BITE FIXING APPLIANCE

[75] Inventors: Ronald J. Sirney, Bloomington; Craig A. Andreiko, Alta Loma, both of Calif.

[73] Assignee: Ormco Corporation, Orange, Calif.

[21] Appl. No.: 09/307,403

[22] Filed: May 7, 1999

[51] Int. Cl.[7] .................................................. A61C 3/00
[52] U.S. Cl. ............................................................. 433/19
[58] Field of Search ........................................ 433/19, 21

[56] References Cited

U.S. PATENT DOCUMENTS

| | | |
|---|---|---|
| 741,687 | 10/1903 | MacDowell . |
| 3,121,953 | 2/1964 | Asher ........................................... 32/14 |
| 3,137,941 | 6/1964 | Andrews ...................................... 32/14 |
| 3,315,359 | 4/1967 | Moss ............................................ 433/5 |
| 3,618,214 | 11/1971 | Armstrong .................................. 32/14 |
| 3,797,773 | 3/1974 | Northcutt .................................... 32/14 |
| 3,997,970 | 12/1976 | Hodgson ..................................... 32/14 |
| 4,121,341 | 10/1978 | DeWoskin ................................... 32/14 |
| 4,439,149 | 3/1984 | Devincenzo ................................. 433/6 |
| 4,462,800 | 7/1984 | Jones ........................................... 433/19 |
| 4,472,139 | 9/1984 | Rosenberg ................................. 433/19 |
| 4,551,095 | 11/1985 | Mason ......................................... 433/19 |
| 4,571,178 | 2/1986 | Rosenberg ................................. 433/18 |
| 4,618,324 | 10/1986 | Nord ........................................... 433/19 |
| 4,708,646 | 11/1987 | Jasper ......................................... 433/19 |
| 4,795,342 | 1/1989 | Jones ........................................... 433/19 |
| 5,120,218 | 6/1992 | Hanson ....................................... 433/19 |
| 5,352,116 | 10/1994 | West ............................................ 433/19 |
| 5,562,445 | 10/1996 | DeVincenzo et al. .................... 433/19 |
| 5,620,321 | 4/1997 | Thornburg et al. ....................... 433/19 |
| 5,632,618 | 5/1997 | Jensen ........................................ 433/19 |
| 5,651,672 | 7/1997 | Cleary et al. .............................. 433/19 |
| 5,697,782 | 12/1997 | Klapper et al. ........................... 433/19 |
| 5,738,514 | 4/1998 | DeVincenzo et al. .................... 433/19 |
| 5,788,486 | 8/1998 | Klapper et al. ........................... 433/19 |
| 5,829,975 | 11/1998 | Gold ........................................... 433/19 |
| 5,846,074 | 12/1998 | Klapper ...................................... 433/19 |

*Primary Examiner*—Todd E. Manahan
*Attorney, Agent, or Firm*—Wood, Herron & Evans, L.L.P.

[57] ABSTRACT

A bite correcting appliance for correcting an overbite or underbite condition of a patient includes upper attachment structure, lower attachment structure and a stretchable, close coil spring connected between the upper and lower attachment structures. The close coil spring exerts a pushing force on the lower jaw as the patient's mouth closes and is substantially non-prestressed or non-preloaded. At least one end of the appliance includes a deformable or crimpable portion allowing selective locking and unlocking to the corresponding attachment structure. Upper and lower attachment members are connected with the close coil spring by both threading and crimping to the spring.

24 Claims, 2 Drawing Sheets

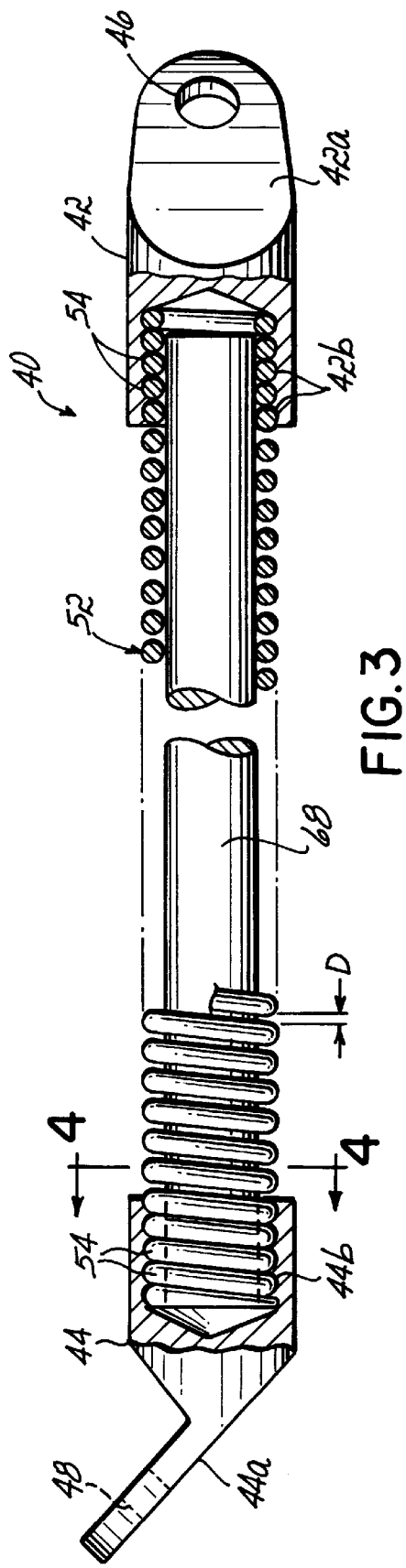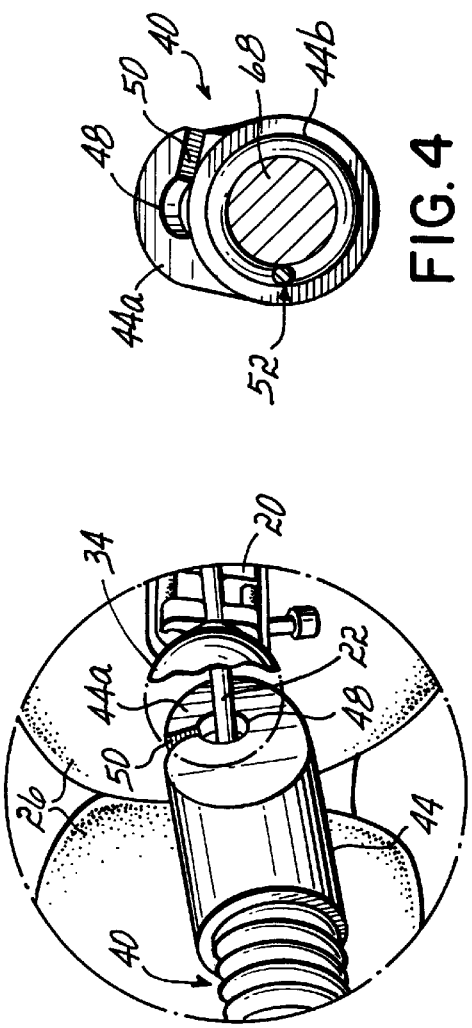

ORTHODONTIC BITE FIXING APPLIANCE

FIELD OF THE INVENTION

The present invention generally relates to orthodontic appliances and, more specifically, to appliances for treating malocclusions of the upper and lower jaws of a patient.

BACKGROUND OF THE INVENTION

Malocclusions between the upper and lower jaws of a patient generally fall within three classes. Class I malocclusions are those in which the individual teeth are not aligning well with each other and with the corresponding teeth in the opposite jaw. This malocclusion is commonly corrected with braces applied to the teeth for gradual realignment. Class II malocclusions relate to those cases in which the lower jaw is not developing in the manner which allows the upper and lower arches of teeth to come together with a proper bite or alignment to one another. More specifically, in this type of malocclusion an overbite condition exists and must be corrected by moving the lower jaw forward to obtain a proper bite. Corrective appliances are therefore used to hold the lower jaw in a proper bite position so that the jaw bones and muscles will support the proper bite. Class III malocclusions occur when the lower jaw is positioned too far forward with respect to the upper jaw. This condition, often referred to as an underbite, is typically corrected with the use of braces and rubber bands and, in some cases, through surgery.

The present invention generally relates to appliances for treating Class II or Class III malocclusions or, respectively, overbite and underbite conditions. In the past, rubber bands and springs extending in tension between upper and lower sets of brackets have been used to move the jaws into alignment as the patient closes their mouth. Over time, this corrective movement will permanently realign the upper and lower teeth of the patient through muscle development and/or proper bone growth. External head gear attached to the braces of the patient has been used for similar purposes. One main disadvantage with these treatment options is that they each require cooperation on the part of the patient. In other words, the patient is required to regularly maintain the rubber bands or head gear in place. Patients may choose not to apply the corrective appliances because they are unsightly or uncomfortable or may forget to apply them. In either case, the lack of diligence in using the corrective appliances reduces the effectiveness of the treatment.

Various bite fixing appliances have also been developed to overcome the disadvantages of rubber bands, springs, head gear or other methods of treating Class II and Class III malocclusions. Several of these appliances involve the use of coil springs connected between upper and lower sets of braces in a patient's mouth. Examples may be found in U.S. Pat. Nos. 3,618,214; 4,708,646; 5,352,116; and 5,846,074. These and other similar bite correcting appliances each suffer from various disadvantages. For example, the appliance described in U.S. Pat. No. 3,618,214 uses superimposed springs to pull a patient's lower jaw forward. This design is prone to mechanical failure and is undesirable for at least this reason. Also, this device is designed to apply a constant pulling force when the patient's mouth is in a closed position and this pulling force increases as the patient opens their mouth. This can be uncomfortable for many patients.

The device disclosed in U.S. Pat. No. 4,708,646 attempted to alleviate some of these concerns, however, the coil spring of this patent is an open coil spring secured within a resilient plastic so as to be nonstretchable. This design is prone to increased incidents of breakage or, in other words, subject to a short fatigue life. The open coil spring and the nonstretchable properties of the appliance increase the amount of stress on the spring and cause the stress to be applied over a shorter length of spring wire. Thus, the spring breaks with undesirable frequency.

U.S. Pat. No. 5,352,116 similarly relates to the use of a sheathed coil spring connected between upper and lower teeth of a patient to provide a pushing force to the lower jaw. As with the appliance shown in U.S. Pat. No. 4,708,646, this appliance can be difficult to install and reinstall. Also, although this appliance uses a stretchable spring, the spring is an undesirable open coil spring design.

U.S. Pat. No. 5,846,074 discloses the use of a coil wire sheath, however, the sheath is configured as an open coil compression spring. This spring presses against opposite connecting pieces as an internal straight wire spring element contained within the sheath is flexed when the mouth moves to a closed position. As stated in the patent, the coil spring does not supply significant pushing force and is not connected to the attachment structure at each end. The function of the coil sheath is to promote comfort and capture any broken pieces of the internal straight wire spring.

In general, the prior bite fixing appliances have provided inadequate treatment options for many patients and even the best appliances are in need of improvement in such areas as increasing fatigue life, easing installation and removal, and simplifying the overall construction.

SUMMARY OF THE INVENTION

The present invention generally relates to a bite correction appliance for overcoming various deficiencies of past appliances. In one aspect, the bite correction appliance of the invention generally includes a first attachment structure adapted to be secured to at least one upper or lower tooth of the patient and a second attachment structure adapted to be secured to a tooth of the opposite jaw which is located in a more forward position. The attachment structures may take many different forms and may be secured to the teeth either directly or indirectly. It is presently contemplated that orthodontic archwires, brackets and auxiliary wires or elements will be used as the attachment structures. In accordance with this aspect of the invention, a stretchable, close coil extension spring is connected between the first and second attachment structures for exerting a pushing force as the patient's mouth closes. When used to correct overbites, the spring will push the lower jaw forward. When used to correct underbites, the spring will push the lower jaw rearward. The close coil extension spring is substantially non-prestressed and includes a maximum gap of 0.015" between adjacent coils in the preferred embodiment. This includes the case in which adjacent coils touch one another.

While typical extension springs may be prestressed or preloaded such that adjacent coils exert forces toward one another, the spring of the present invention is substantially non-prestressed. This, along with the additional wire resulting from the use of a close coil spring design, provides a longer fatigue life for the spring. In the preferred embodiment, the maximum gap between adjacent coils is 0.010" and, more preferably, 0.005".

To further increase the fatigue life of the spring, the spring is formed from double vacuum melted stainless steel. Another advantageous material for the spring is superelastic material such as nickel titanium. At least some of the adjacent coils are preferably exposed or not encased in other structure. This allows stretching of the extension spring during use. The appliance further comprises a flexible rod, such as a polymeric rod, contained within the adjacent coils. This rod prevents food from being entrapped with the spring and provides some support for the coil spring.

In another aspect of the invention, a coil spring assembly is formed with first and second attachment members affixed to opposite ends of the spring. The first attachment member is connected with the first attachment structure and the second attachment member is connected with the second attachment structure. At least one of the attachment members includes a connecting portion movable between locked and unlocked positions relative to its corresponding attachment structure. This allows at least one end of the spring to be selectively attached to and released from attachment structure, such as an archwire. In the preferred embodiment, the connecting portion is a deformable portion communicating with a hole in the first and/or second attachment member. This deformable portion may be moved between the locked and unlocked positions to allow connection and disconnection with respect to the corresponding attachment structure.

As another aspect of the invention, the first and second attachment members are threaded onto respective first and second ends of a coil spring, such as the close coil extension spring of the invention. After being rotated to the proper orientation with respect to one another, each of the attachment members is crimped to the coil spring to prevent further rotation relative to the coil spring. In this manner, flat connecting portions may be oriented, for example, approximately 90° with respect to each other about the axis of the spring.

These and various other objectives, advantages and features will become more readily apparent to those of ordinary skill in the art upon review of the following detailed description of the preferred embodiment, taken in conjunction with the accompanying drawings.

BRIEF DESCRIPTION OF THE DRAWINGS

FIG. 2A is an enlarged view of encircled portion 2A in FIG. 2;

FIG. 3 is a partially fragmented, side elevational view of the coil spring assembly of the appliance; and FIG. 4 is a cross sectional view taken along line 4—4 of FIG. 3.

DETAILED DESCRIPTION OF THE PREFERRED EMBODIMENTS

Figure 1:
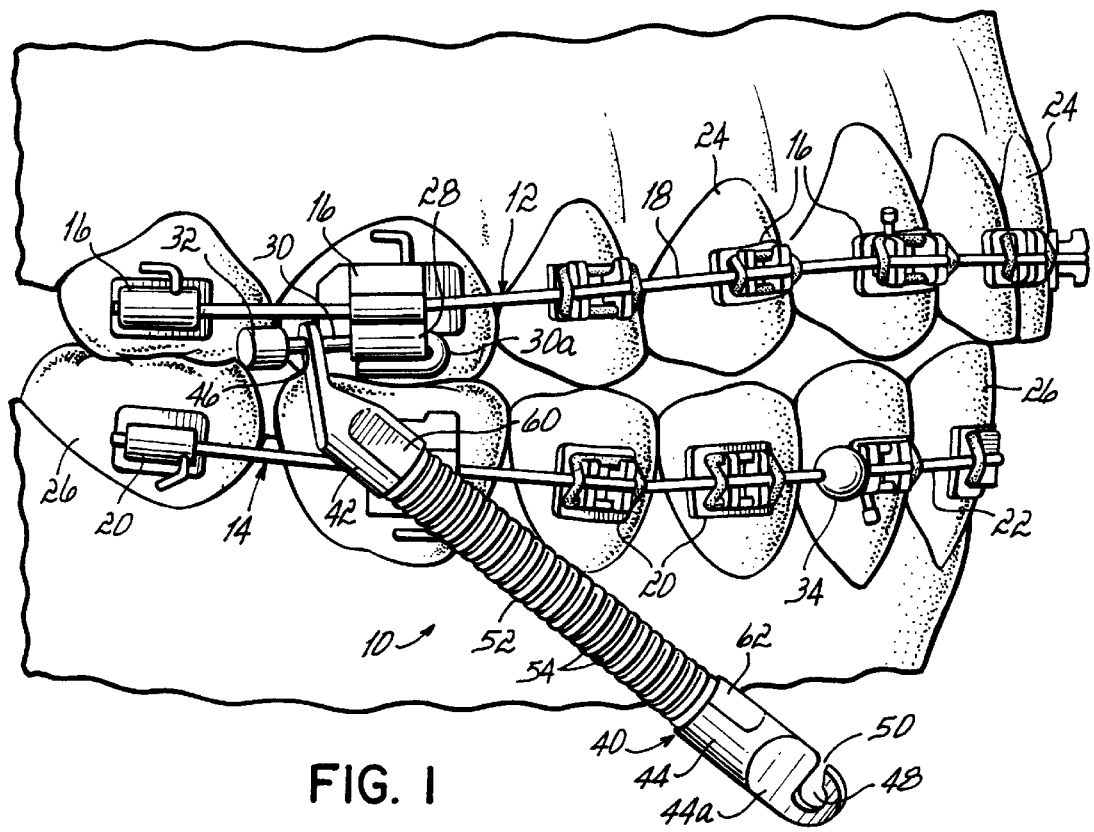
FIG. 1 is a side elevational view of an appliance constructed in accordance with the preferred embodiment and shown partially connected to the braces of a patient.
Figure 2:
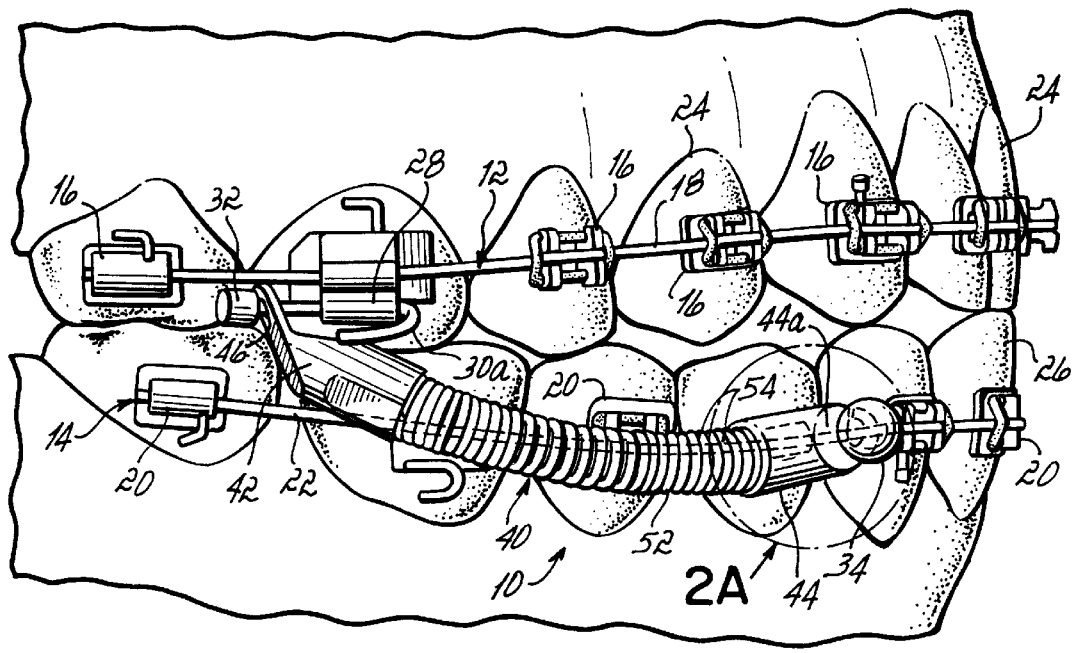
FIG. 2 is a side elevational view similar to FIG. 1, but showing the appliance fully connected and correcting an overbite condition of the patient.

Referring generally to FIGS. 1 and 2, an appliance 10 is shown constructed in accordance with one preferred embodiment of the invention. Appliance 10 will be shown and described with respect to this preferred embodiment in terms of a device for correcting an overbite condition or Class II malocclusion. Those of ordinary skill in the art will readily appreciate that the device is easily adapted to correct underbite conditions or Class III malocclusions as well. Generally, the upper and lower connections of the device merely need to be reversed to reconfigure appliance 10 as a Class III corrective device. Other modifications of the structure and use of appliance 10 are also within the scope of the inventive concepts as will become more readily apparent upon reading the description of this preferred embodiment.

Appliance 10 generally includes upper attachment structure 12 and lower attachment structure 14. In a typical case, this will include upper brackets 16 connected with an upper archwire 18 and lower brackets 20 connected with a lower archwire 22. These comprise typical braces secured to upper and lower teeth 24, 26 of a patient. Other attachment structures may be substituted to perform this connecting function, for example, when braces are not worn by the patient. As shown in FIG. 1, the lower teeth 26 and lower jaw of the patient have an underbite with respect to the upper teeth 24 and upper jaw. A bracket 16 at the rear of the patient's mouth includes a tube 28 receiving a pin 30 having a hook-shaped portion 30a. A ball or stop member 32 is disposed on the opposite end of pin 30. A similar ball or stop member 34 is contained on lower archwire 22 at a more forward position. Appliance 10 further includes a close coil extension spring assembly 40 connected between the upper and lower attachment structures 12, 14. More specifically, upper and lower attachment members 42, 44 are respectively connected to pin 30 and archwire 22 (FIG. 2). Thus, as the patient's mouth closes to the position shown in FIG. 2, a pushing force is exerted to the lower jaw in a forward direction against stop member or ball 34. If a corrective device for Class III malocclusions is desired, then upper attachment member 42 would be connected to a lower tooth and lower attachment member 44 would be connected to an upper tooth. This would provide a forward pushing force to the upper jaw and a rearward pushing force to the lower jaw during mouth closure.

Referring to FIGS. 3 and 4, upper and lower attachment members 42, 44 each include flat portions 42a, 44a and internally threaded portions 42b, 44b. Flat portions 42a, 44a include respective holes 46, 48 for connection with archwires 18, 22 (FIGS. 1 and 2). Hole 48 contained in flat portion 44a communicates with a slot 50 for attachment purposes as will be described below. FIG. 3 illustrates flat portions 42a, 44a in a preferred orientation rotated approximately 90° apart relative to the longitudinal axis of assembly 40. Close coil spring 52 is formed by coils 54 either touching or spaced very closely apart by a gap D. Gap D is preferably less than 0.015" and, most preferably, less than 0.005". As shown in FIG. 3, coils 54 at opposite ends of spring 52 are threaded into threaded portions 42b, 44b of members 42, 44. These coils are also very closely spaced or touching as previously described. A flexible rod 68 is contained with a close fit within spring 52. Rod 68 may be formed of polyurethane and provides support for spring 52. Rod 68 also prevents food from becoming trapped in spring 52.

As best shown in FIG. 1, after attachment members 42, 44 are rotated to the proper orientation by threading onto the ends of spring 52, attachment members 42, 44 are lightly crimped as indicated by crimps 60, 62 to retain the desired orientation. The crimping is preferably not forceful enough to retain members 42, 44 on the ends of spring 52 since the threading action will provide this function in a less stressful manner. Crimps 60, 62 are simply used to prevent further rotation of attachment members 42, 44 with respect to spring 52 as such rotation would inhibit the desired swivelling characteristics of spring assembly 40 during use.

Appliance 10 may be affixed to teeth 24, 26 in various manners other than the one shown in the drawings. Referring to FIG. 2, as one preferred manner, attachment member 44 is applied to lower archwire 22 by hooking archwire 22 into hole 48 and crimping flat portion 44a to a closed or locked position as shown in FIG. 2A. Within this configuration, slot 50 is not large enough to allow archwire 22 to escape from hole 48. The opposite attachment member 42 is then connected with pin 30 by sliding pin 30 through hole 46. Pin 30 is then inserted into tube 28 and bent to form hook-shaped end 30a. The distance of stop member or ball 32 from tube 28 may be adjusted to some extent to adjust the amount of forward pushing force provided by appliance 10. To make this adjustment, pin 30 may be straightened and moved to the right or left as viewed in FIG. 2 and end 30a may be rebent to retain the adjusted position.

Thus, it will be appreciated that a forward pushing force on the lower jaw will be exerted through coil spring 52 as spring assembly 40 is retained between stop members 32 and 34 during mouth closure. When the patient's mouth is opened, spring 52 will stretch to some extent to relieve stress in the opposite direction. To remove coil spring assembly 40, lower flat portion 44a is uncrimped or moved to an unlocked position as shown in FIG. 1 allowing removal from archwire 22. Pin 30 may then be either clipped or straightened to allow removal from tube 28. A new appliance 10 may then be easily applied in the manner described above. This aspect of the invention avoids the necessity to cut the archwire to remove the appliance. It will be appreciated that other quick release connectors are within the scope of this invention as well.

While the present invention has been illustrated by a description of the preferred embodiment and while this embodiment has been described in some detail, it is not the intention of the Applicant to restrict or in any way limit the scope of the appended claims to such detail. Additional advantages and modifications will readily appear to those skilled in the art. This has been a description of the present invention, along with the preferred methods of practicing the present invention as currently known. Various aspects of this invention may be used alone or in different combinations. The scope of the invention itself should only be defined by the appended claims, wherein we claim:

What is claimed is:

1. A bite correction appliance for correcting an overbite or underbite condition of a patient, the appliance comprising:

first attachment structure adapted to be secured to at least one upper tooth of the patient, second attachment structure adapted to be secured to at least one lower tooth of the patient with one of the first and second attachment structures located forward of the other, and a stretchable, close coil extension spring connected to the first and second attachment structures for exerting a pushing force in a direction suitable to correct the overbite or underbite condition as the patient's mouth closes, said close coil extension spring being substantially non-prestressed and having adjacent coils spaced with a maximum gap of 0.015".

2. The appliance of claim 1, wherein the maximum gap is 0.010".

3. The appliance of claim 1, wherein the maximum gap is 0.005".

4. The appliance of claim 1, wherein said close coil extension spring is formed from double vacuum melted stainless steel.

5. The appliance of claim 1, wherein said close coil extension spring is formed from superelastic material.

6. The appliance of claim 1, wherein at least some of the adjacent coils are exposed and the appliance further comprises a flexible rod contained within the adjacent coils.

7. The appliance of claim 1, wherein the close coil extension spring further includes first and second ends and further comprising first and second attachment members threaded onto the respective first and second ends and crimped to prevent rotation relative to the spring, said attachment members being operative to connect said spring to the respective first and second attachment structures.

8. The appliance of claim 1, wherein the first attachment structure includes an archwire and a first attachment member is connected with a first end of the spring, said first attachment further including a connecting portion movable between locked and unlocked positions relative to the first attachment structure, whereby the first end of the spring may be selectively attached to and released from the archwire.

9. The appliance of claim 8, wherein the connecting portion is a deformable portion communicating with a hole in said first attachment member, said hole being adapted to receive said archwire.

10. A bite correction appliance for correcting an overbite or underbite condition of a patient, the appliance comprising:

first attachment structure adapted to be secured to at least one upper tooth of the patient, second attachment structure adapted to be secured to at least one lower tooth of the patient with one of the first and second attachment structures located forward of the other, and a coil spring having a first attachment member connected with the first attachment structure and a second attachment member connected with the second attachment structure such that a pushing force is exerted by the coil spring in a direction suitable to correct the overbite or underbite condition as the patient's mouth closes, at least one of said first and second attachment members including a connecting portion movable with respect to another portion of said one attachment member between locked and unlocked positions to selectively attach said one attachment member to a corresponding one of said first and second attachment structures and selectively release said one attachment member from the corresponding one of said first and second attachment structures.

11. The appliance of claim 10, wherein the first attachment structure includes an archwire adapted to be connected with a plurality of brackets.

12. The appliance of claim 10, wherein the connecting portion is a deformable portion communicating with a hole in said first attachment member.

13. The appliance of claim 10, wherein said coil spring is formed from double vacuum melted stainless steel.

14. The appliance of claim 10, wherein said coil spring is formed from superelastic material.

15. The appliance of claim 10, wherein at least some of the coils of said coil spring are exposed and the appliance further comprises a flexible rod contained within the adjacent coils.

16. The appliance of claim 10, wherein the first and second attachment members are threaded onto respective first and second ends of the coil spring and said first and second attachment members are further crimped to said first and second ends to prevent rotation relative to the spring.

17. The appliance of claim 10, wherein said coil spring is an extension spring and is stretchable while exerting said pushing force.

18. A bite correction appliance for correcting an overbite or underbite condition of a patient, the appliance comprising:

first attachment structure adapted to be secured to at least one upper tooth of the patient, second attachment structure adapted to be secured to at least one lower tooth of the patient with one of the first and second attachment structures located forward of the other, and a coil spring having a first attachment member at a first end connected with the first attachment structure and a second attachment member at a second end connected with the second attachment structure such that a pushing force is exerted by the coil spring in a direction suitable to correct the overbite or underbite condition as the patient's mouth closes, said first and second attachment members being threaded onto the respective first and second ends of said coil spring and further being crimped to the coil spring to prevent rotation thereof relative to the coil spring.

19. The appliance of claim 18, wherein the coil spring includes an axis and each of the first and second attachment members include flat portions, said first and second attachment members being crimped to the coil spring in orientations disposed approximately 90° apart relative to the axis of the coil spring.

20. The appliance of claim 19, wherein the flat portion of the first attachment member includes a selectively lockable connecting portion for engagement and disengagement with respect to the first attachment structure.

21. The appliance of claim 20, wherein the selectively lockable connecting portion is a crimpable member positioned adjacent to a hole in the flat portion of said first attachment member.

22. The appliance of claim 18, wherein said coil spring is an extension spring and is stretchable while exerting said pushing force.

23. The appliance of claim 18, wherein said coil spring is formed from double vacuum melted stainless steel.

24. The appliance of claim 18, wherein said coil spring is formed from superelastic material.

* * * * *